Figure 1:
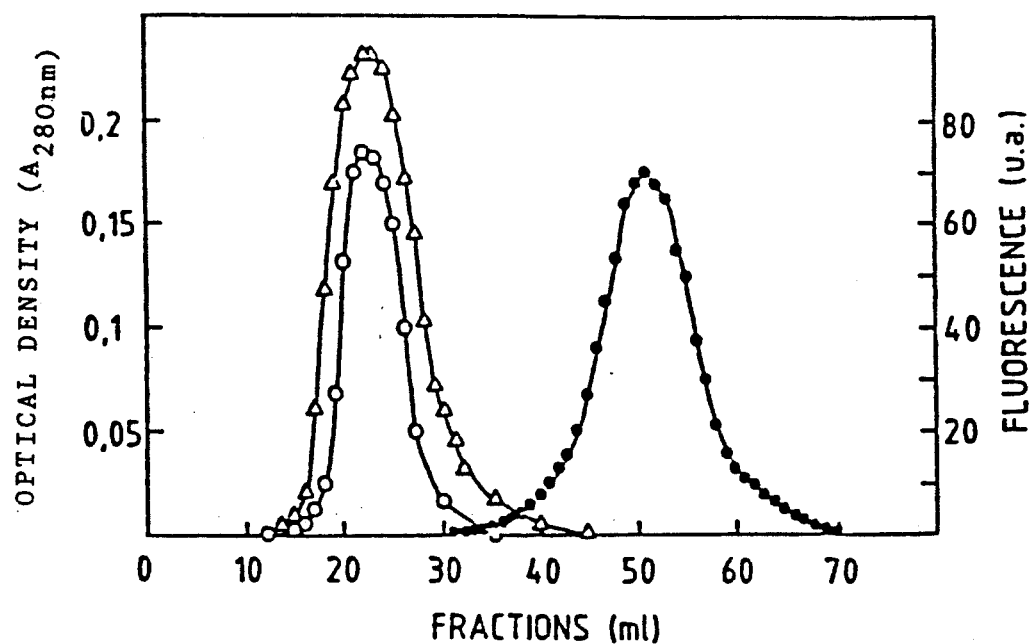

United States Patent [19]

Di Giambattista et al.

[11] Patent Number: 5,200,394
[45] Date of Patent: Apr. 6, 1993

[54] DERIVATIVES OF TYPE A AND B SYNERGIMYCINS

[76] Inventors: Mario Di Giambattista, 38, Av. de Mai, 1200, Brussel; André Pecher, Ave. Télémaque 8 bte 10, 1190 Brussels; Carlo Cocito, Rue de l'Elevage 26, 1340 Bruyeres/Ottignies, all of Belgium

[21] Appl. No.: 474,806
[22] PCT Filed: Oct. 21, 1988
[86] PCT No.: PCT/BE88/00029
    § 371 Date: Jun. 22, 1990
    § 102(e) Date: Jun. 22, 1990
[87] PCT Pub. No.: WO89/03843
    PCT Pub. Date: May 5, 1989

[30] Foreign Application Priority Data

Oct. 22, 1987 [BE] Belgium .................. 8701199

[51] Int. Cl.$^5$ .............. A61K 37/00; A61K 37/02; C07K 7/02; C07K 5/00
[52] U.S. Cl. ........................ 514/9; 514/11; 514/17; 514/16; 514/375; 530/317; 530/329; 530/330
[58] Field of Search ............ 514/9, 11, 17, 16, 375; 530/317, 329, 330

[56] References Cited

FOREIGN PATENT DOCUMENTS 0117934 9/1984 European Pat. Off. .
8903843 5/1989 PCT Int'l Appl. .

OTHER PUBLICATIONS

The Merck Index, ed. 10, 1983, p. 1432 Abst. No. 9810 "Virginiamycin".

*Primary Examiner*—Merrell C. Cashion, Jr.
*Assistant Examiner*—A. M. Davenport
*Attorney, Agent, or Firm*—Hayes, Soloway, Hennessey & Hage

[57] ABSTRACT

The invention synergimicin derivatives having the general formula: Z—X—R, in which Z is a type A or type B synergimycin radical linked by its reactive carbonyl position, through a branch X, where X is =N— or =N—O—, to a substituted R, where R is a hydrogen atom, an alkyl group, an alkyl-COOH group, an -alkyl-($\alpha NH_2$)COOH group (I), group (II), group (III) or a group (IV), where n is a function of the number of —$NH_2$ groups present on the coupling protein. Also described are the salts, esters and possibly addition products of pharmaceutically acceptable acids. The invention also concerns a process for preparing these substances, and their use.

21 Claims, 7 Drawing Sheets 1. 22 µg (VS)$_{15}$—BSA
2. 11 µg (VS)$_{15}$—BSA
3. 7 µg (VS)$_{15}$—BSA
4. 22 µg BSA
5. 15 µg IGg anti-VS

DERIVATIVES OF TYPE A AND B SYNERGIMYCINS

OBJECT OF THE INVENTION

The present invention concerns derivatives of synergimycin, more specifically virginiamycin S and derivatives of virginiamycin M. It also relates to a process for the preparation of these derivatives. Further, their uses in human and veterinary medicine, and for the production of antibodies against the above antibiotics are also described.

OUTLINE OF TECHNICAL BACKGROUND

Virginiamycins S and M belong to a family of antibiotics generally known under designations such as "synergistins", "synergimycins" and "streptogramins". These antibiotics, as produced by streptomycetes, are mixtures of two types of compounds, A and B, which in vivo display a synergistic activity. Type A compounds from different microorganisms are similar as well as the type B compounds. However, the structures of A and B compounds are different.

Numerous work on these antibiotics have been published and several products are available under different commercial names (cf. the Merck Index, 10th ed., 1983, Merck & Co, Inc., Rahway, N.J., US, pag. 1432, Nx9810 "Virginiamycin").

Techniques for production of antigenic modification of polypeptides capable of inducing the formation of antibodies are also known (cf., e.g., EP, A, 0117934, The Ohio State University, Sep. 12, 1984, pag. 1–7).

DISADVANTAGES OF THE KNOWN PRODUCTS

In spite of the fact that an A+B mixture is more powerful than most antibiotics, the medical use of synergimycins has been limited by their poor water solubility. In fact, the level of absorbtion as from the intestin is very low and the blood-to-tissue partition coefficient is unfavorable.

AIMS OF THE PRESENT INVENTION

The aim of the present invention is to provide derivatives of natural products of the type A and B synergimycins, and more specifically of virginiamycins M and S.

An other aim of the present invention is to provide derivatives of the above mentioned type having a modified solubility in aqueous media, thus allowing the attainment of higher concentrations in blood and tissues.

A complementary aim consists in providing derivatives of virginiamycin and more particularly virginiamycin S and M showing a high therapeutic activity in the case of microbic diseases, resulting from their intrinsic properties.

According to another aspect, the present invention provides a process for the preparation of said derivatives as from natural products, which are produced by appropriate streptomycetes.

According to a complementary aspect of the present invention concerns uses of said antibiotics in human and veterinary medicine and for the production of antibodies directed against virginiamycins.

DESCRIPTION OF THE PRINCIPLES OF THE INVENTION

The derivatives of synergimycin which are dealt with by the present invention are those selected from the group consisting of compounds of general formula Z—X—R where Z is a synergimycin radical of type A or B which is linked through its reactive carbonyl and by means of an arm of the type =N— or =N—O— to a substituent R representing a hydrogen atom, an alkyl group, an alkyl-COOH group, an alkyl ($\alpha$—NH$_2$-)COOH group, an

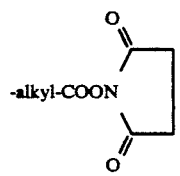

group, an

group, an (-alkyl-CO—NH)$_n$ protein group or an (-alkyl-CONH)$_n$⊢ribosome group where n is a function of the NH$_2$ content of the coupling protein as well as pharmaceutically acceptable salts, esters and, optimaly, acid addition compounds with pharmaceutically acceptable acids.

The invention concerns more particularly derivatives of synergimycin of the above defined type wherein Z represents the virginiamycin M radical of formula

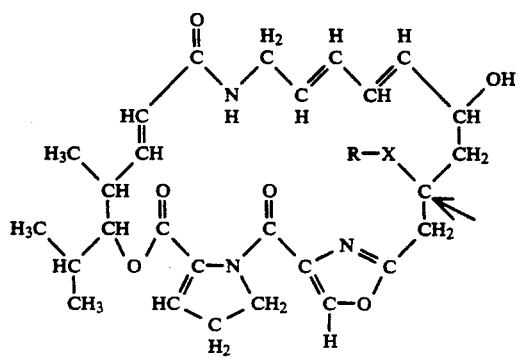

and the virginiamycin S radical of formula

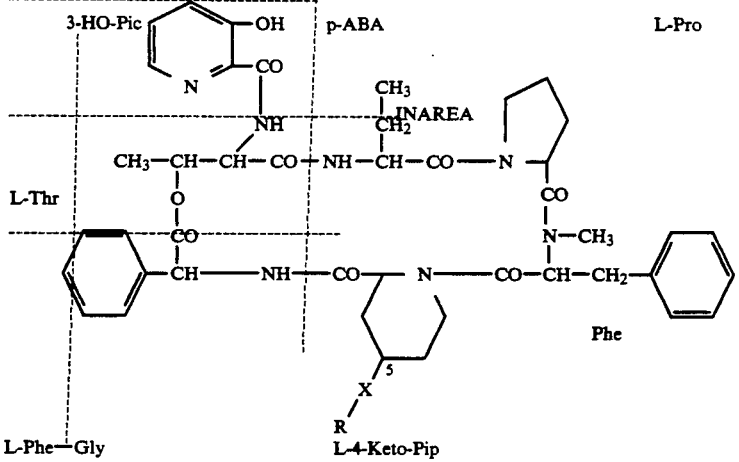

X and R being as already defined.

It has been noted that the derivatives of the invention are biologically active and have a water/organic solvents partition coefficient more favorable than those of the starting products.

According to the present invention derivatives of the type Z=N—O—R, which are endowed with higher stability in aqueous media are preferred.

It should further be noted that the activity of the thus obtained antibiotics on a given target may be further increased by choosing the appropriate R substituents linked to the natural product via the arm X.

According to another aspect of the present invention the above defined derivatives are obtained by reacting a compound of the type NH$_2$—R or NH$_2$—O—R, where R is a hydrogen atom, a linear or branched alkyl group, an alkyl-COOH group or an alkyl-(α-NH$_2$)COOH group with the starting compound of compounds obtained by streptomycetes at a temperature between 20° C. and 30° C., preferably at a temperature of about 20° C., for 1 to 12 hours, preferably about 4 hours, in pyridine medium.

The product thus obtained may be reacted with a compound of the type

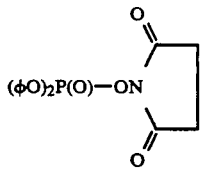

at a temperature between 10° and 30° C., preferably of about 20° C. for 12 to 48 hours, preferably 24 hours, in the presence of triethylamine.

The product thus obtained is suitable for coupling synergimycins to a protein or a ribosome.

It may also be reacted with every compound containing a NH$_2$ group.

The derivatives according to the present invention may be used individually or in combination with one another, for instance a A-type derivative and a B-type derivative for the preparation of pharmaceutical compositions, optionally in combination with other pharmaceutically acceptable compatible active substances as well as with vehicles, excipients and/or solvents.

The derivatives according to the present invention bearing a protein radical are suitably used for production of antibodies directed against the antibiotic, hence the use of these compounds for diagnostic and/or determination of the presence of and quantitative determination of the antibiotic, particularly by enzymatic determination.

EMBODIMENTS OF THE INVENTION

The invention is described more precisely with reference to the following examples.

Analytical grade reagents are used. Thin layer chromatographies are carried out on 0.2 mm silica gel (aluminum) 60F254 (Merck).

EXAMPLE 1

Synthesis of the N-Hydroxysuccinimide Derivative of Virginiamycin S (VS Ester)

This synthesis occurs in 3 steps: 1) synthesis of the SDPP reagent; 2) the carboxylic derivative of VS and 3) the activated ester of VS.

A. Method

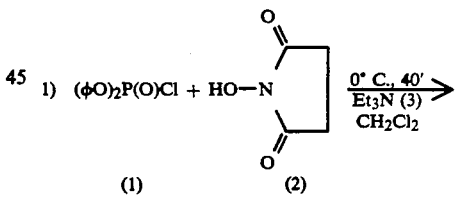

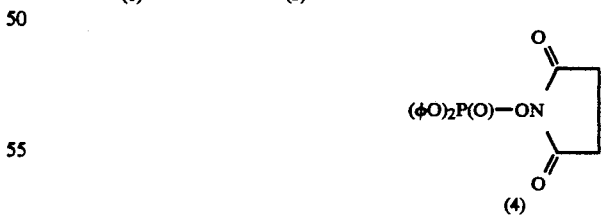

Reaction

To 0.01 mole of compound (2) in 6 ml dry (CH$_2$Cl$_2$) (molecular sieve 4 Å+P$_2$O$_5$) the following reagents are slowly added, under agitation and in the order, at 0° C.: 0.01 mole of (3) and 0.01 mole of (1) in 6 ml dry CH$_2$Cl$_2$. Agitation is pursued for 15 min at 0° C., and CH$_2$Cl$_2$ is evaporated under reduced pressure at 40° C. The residue is treated with 50 ml ether yielding a white precipitate, which is filtered, washed with 20 ml ether, dried and dissolved in 100 ml ethylacetate. The organic phase is washed thrice with 10 ml H$_2$O at 0° C. and dried on molecular sieve 4 Å. The ethyl acetate layer is evaporated to dryness under reduced pressure at 40° C. A crystalline product is obtained in a 90% yield.

B. Characterization

Thin layer chromatography on 0.2 mm silica gel 60F254 aluminum plate (Merck)

| | | RF |
|---|---|---|
| CHCl$_3$/MeOH/HAC | (1) DPCl: | 0,05 |
| 95:4:4 | (2) NHS: | 0,165 |
| | (4) SDPP: | 0,57 |

Synthesis of reagent SDPP (compound 4) and its characterisation are described (Ogura H. et al., Tetrahedron Letters, 1980, 21, 1467-1468).

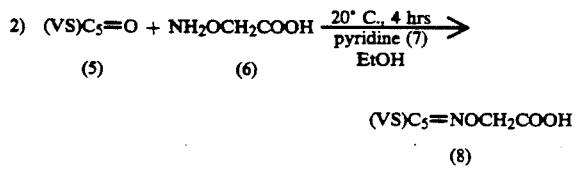

C. Reaction

To 0.001 mole of (5) in 20 ml ethanol the following reagents are added, in this order: 250 μl pyridine, and then slowly 0.004 moles of (6) in 20 ml ethanol. Agitation is pursued for 4 h at room temperature.

The solvent is evaporated to dryness under reduced pressure at 40° C. The residue is then diluted in 25 ml 0.25N HCl. The aqueous phase is extracted with four 20 ml-aliquots of distilled H$_2$O and dried on 4 Å molecular sieve. The chloroform is evaporated to dryness under reduced pressure at 40° C. Crystalline product obtained in a 80% yield.

D. Characterization

Thin layer chromatography

| CHCl$_3$/MeOH/HAC | (5) | (VS)C$_5$=O: | 0,62 |
|---|---|---|---|
| 95:4:4 | (8) | VSCOOH: | 0,32 |

$^1$H-NMR: 4.52–4.56 ppm (2H, α-COOH)

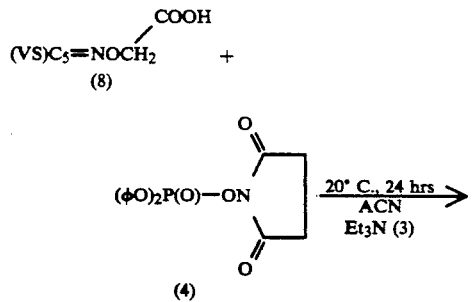

E. Reaction

To 0.0001 mole of (8) in 1 ml acetonitrile, the following reagents are added, in the order, and under agitation: 0.0005 moles of (3) and slowly 0.0005 moles of (4) in 2 ml acetonitrile. Agitation is pursued for 24 h at room temperature, in dark. The product is stored at 4° C., in dark, in acetonitrile.

F. Characterization

1) Thin layer chromatography

| | | RF |
|---|---|---|
| CHCl$_3$/MEOH/HAC | (8) VSCOOH: | 0,32 |
| 95:4:4 | (4) SDPP: | 0,57 |
| | (9) VS ESTER: | 0,50 |

2) $^1$H NMR: 2.86 ppm (4H, O-succinimide)

EXAMPLE 2

Coupling of Virginiamycin S with Bovine Serum Albumin

Bovine serum albumin (BSA) is a molecule possessing about 52 residues of lysine per mole (52 ε-NH$_2$ groups) which readily react with the activated ester of virginiamycin S. The bovine serum albumin used has 99% purity.

Method

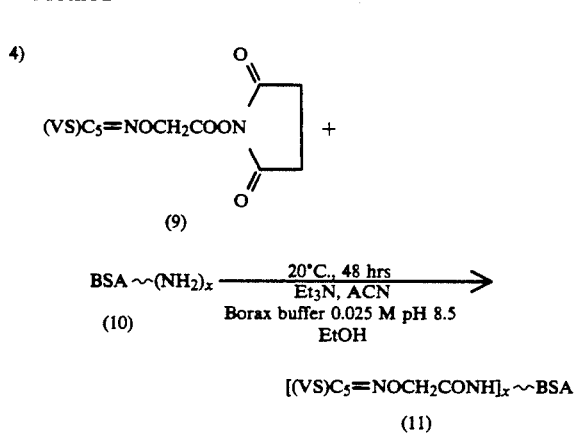

A. Reaction

To 1.43 μmoles of (9) in 100 μl acetonitrile, the following reagents are added, under agitation and in the order: 2 μl of (3); 150 μl of EtOH, 150 μl of 0.025M borax buffer pH 8.5; 100 μl of a solution containing 10 mg/ml BSA (14.3 nmoles) and 200 μl EtOH. Agitation is pursued in dark for 48 h, under CaCl$_2$, at room temperature.

B. Purification of (VS)$_x$ — BSA (FIG. 1)

At the end of the reaction, the coupling product (VS)$_x$ — BSA is precipitated at $-70°$ C. for 1 h with 50 μl 2M KCl and 8 ml EtOH. After centrifugation, supernatant is discarded and precipitate is dried.

The residue is dissolved in 1 ml distilled H2O; the procedure is repeated twice (precipitation, centrifugation, drying of residue). Precipitate is dissolved in 1 ml distilled H$_2$O and 40 μl 10M urea. This sample is fractionated on a Sephadex G150 column, which is eluted with a 4.8×10$^{-2}$M NaH$_2$PO$_4$/0.1M NH$_4$Cl solution.

Fractions of 1 ml are collected and those showing a A260 absorbance are concentrated to ±1 ml on polyethylene glycol. The sample is then dialyzed for 12 h at 4° C. against 500 ml 0.1N NaCl. Dialysate is finally lyophilyzed and stored at $-20°$ C.

C. Evaluation of the coupling yield

1) The lyophilyzed preparation is dissolved in 1 ml distilled H$_2$O, and total proteins (BSA) are measured by the Lowry's procedure (24) on a calibration curve within the 4 to 20 µg/ml range.

2) The fluorescence intensity of the sample is measured by an Aminco-Bowman SPF Ratio II spectrofluorimeter ($\lambda exc=330$ nm; $\lambda emiss=420$ nm) and compared under the same analysis conditions to the fluorescence of a virginiamycin S sample of known concentration.

The total concentration of virginiamycin S in the sample is deduced.

3) The yield of coupling is calculated by the relationship $$yield = \frac{total\ VS\ concentration}{total\ BSA\ concentration} = \frac{mole\ VS}{mole\ BSA}$$

4) The coupling yield, as a function of the (VSE)/(BSA) ratio at the starting point of the reaction, has been examined and displayed in FIG. 1. Yield varies between 5 and 35 moles VS/mole BSA. Under the reaction conditions described in A, a yield of $15\pm3$ moles VS/mole BSA is generaly obtained.

D. Characterization of (VS)15 BSA

1) Thin layer chromatography

| CHCl$_3$/MeOH/HAC | | Rf | FLUO |
|---|---|---|---|
| 95:4:4 | (10) BSA | 0 | — |
|  | (9) VS ESTER | 0,5 | + |
|  | (11) (VS)$_{15}$ BSA | 0 | + |

Figure 2:
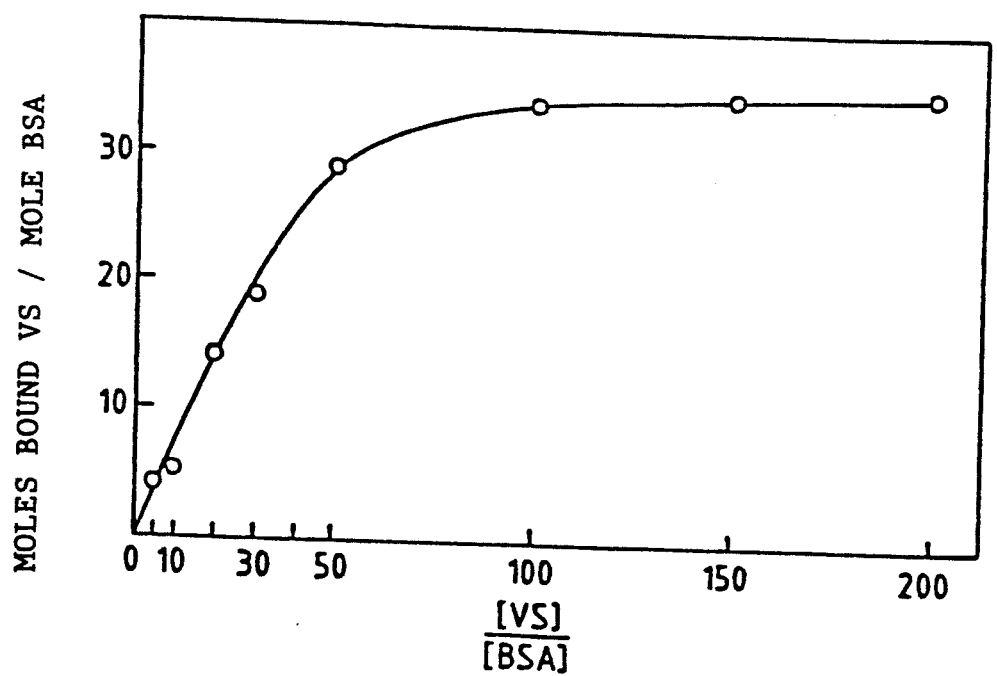

2) Chromatography on Sephadex column G150 (FIG. 2)

a) The standard sample of virginiamycin S is recovered between fractions 30 and 70 ml.

b) The standard BSA sample (4 mg/ml) is recovered under the same conditions between 10 and 30 ml. No fluorescence is noted in this case.

c) The purified sample (VS)$_{15}$ BSA (4 mg/ml) is obtained under the same conditions in fractions 10 to 30 ml.

A fluorescence is noted in this case. This analysis shows the stability of the (VS)$_{15}$ BSA derivative, which has withstood all purification steps.

Figure 3:
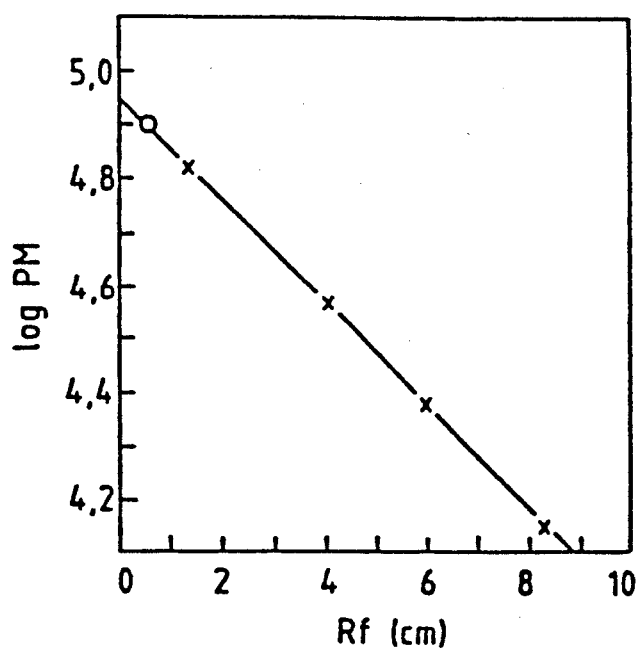

3) Electrophoresis on SDS-polyacrylamide gel (FIG. 3)

a) Several proteins of known molecular weight (including BSA) are fractionated on a SDS-polyacrylamide gel (25). The more a protein migrates with an important Rf, the less is its molecular weight.

b) (VS)$_{15}$ BSA is analyzed likewise: its Rf yields a measurement of its size (79.200).

c) Compared to the molecular weight of BSA and knowing the molecular weight of virginiamycin S, a coupling yield of $15\pm3$ moles VS/1 mole BSA has been calculated, a result confirming those in C 4).

EXAMPLE 3

Production of Antibodies Against Virginiamycin S.

A. Immunisation

1) Anti-VS antibodies are generated by immunisation of two New Zealand rabbits with (VS)$_{15}$ BSA.

2) The injections are preformed subcutaneously according to the following protocol:

a) a first dose of 0.5 mg in 500 µl physiologic H$_2$O plus 500 µl complete Freund adjuvant (ten 100-µl administrations).

b) at day 8, a double dose is administrated, 1 mg in 500 µl physiologic H$_2$O plus 500 µl incomplete Freund adjuvant.

c) a new dose of 0.5 mg is administered at days 15 and 22 as in b).

3) Blood is collected by ear puncture a) 20 ml, before injection (control serum)

b) 50 ml, 7 days after the 2nd injection c) 50 ml, 7 days after each booster injection, at 3 weeks interval.

4) Serum is obtained by centrifugation of the blood at 3000 rpm for 5 min. Supernatant is withdrawn and serum stored at $-20°$ C.

B. Extraction of total serum IgG

1) A DEAE affi-gel blue (Bio-Rad) column is prepared in that purpose. A volume of 7 ml support is used for purification of one ml serum.

2) This column is equilibrated with 2 volumes buffer A (0.02M Tris-HCl pH 8.0; 0.028M NaCl; 0.02% NaN$_3$).

3) Serum is dialyzed against buffer A.

4) The dialysate is loaded on the column and eluted with 3 volumes buffer A.

Fractions of 1–2 ml are collected and spectrophotometrically at 280 nm. The fractions showing an absorbance are pooled and concentrated to 1 ml on polyethylene glycol.

5) The column is then regenerated with 2 volumes of 6M guanidine.HCl or with 6M NaSCN followed by 2 volumes buffer A.

C. Purification of VS-specific immunoglobulins (anti-VS).

1) Coupling of virginiamycin S with Affi-gel 102.

Affi-gel 102 (Bio-Rad) is a branched agarose gel carrying terminal —NH$_2$ functions. According to specification, there are 15 moles —NH$_2$/ml gel.

a) Structure

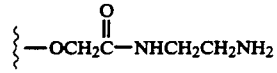

b) Sheme of reaction

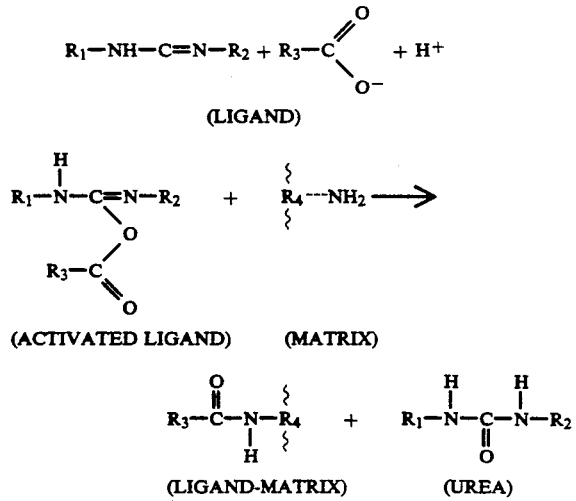

c) Reaction 1) 30 mg VS.COOH are dissolved in 5 ml EtOH and 1 ml H$_2$O at pH 4.5 (0.1N HCl) (solution A).

2) 21 mg EDC are dissolved in 2 ml $H_2O$ at pH 4.5 (HCl 0.1N) (solution B).

3) Solution A is added to 10 ml Affi-gel 102, under agitation, in dark.

200 μl-portions of solution B are added at 2 min intervals. Reaction is pursued at room temperature, under agitation in dark, for 20 h.

2) Preparation of an affinity column Affi-gel 102-VS a) 5 ml of the reaction product in 1)c are loaded on a 10 ml column;

b) the column is washed and conditioned with 50 ml EtOH/$H_2O$ (50:50 mixture), followed by 40 ml buffer A (B 2).

3) Isolation of VS-specific IgG a) the total concentrated IgG fraction as in B is loaded on the affinity column and eluted with buffer A until no absorbing recovered fraction is found (non-specific IgG are eliminated).

b) virginiamycin S-specific IgG adsorbed on the column are detached by a solution of 50 mM glycine.HCl pH 2.8. The fractions having an optic density of more than 0 are pooled and dialysed against buffer A (12 hours, 4° C.). The specific IgG are then concentrated on polyethylene glycol.

c) the concentration of immunoglobulins is estimated by Bradford's method. They are stored at −20° C.

D. Characterization of anti-VS immunoglobulins

Figure 4:
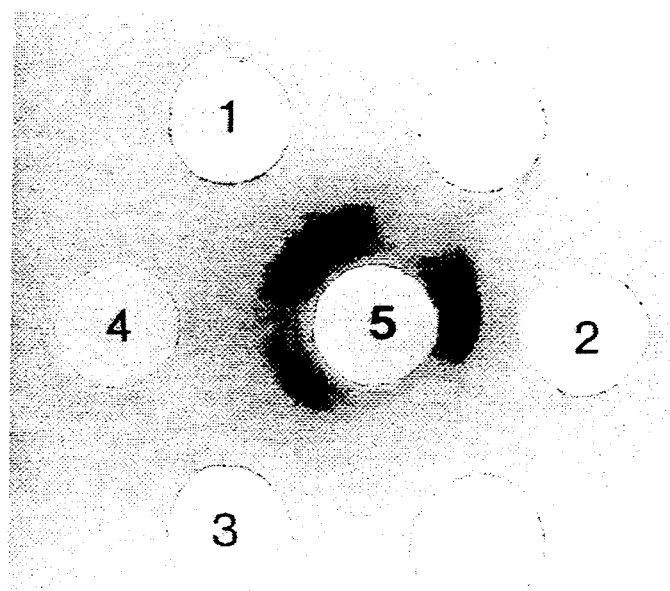

1) Immunodiffusion (Ouchterlony). (FIG. 4)

a) an agarose film (1% agarose in 0.1M NaCl, 0.05M Tris-HCl pH 7.5, 0.1 nM EDTA) is poored on a glass plate.

b) six holes around a central well are carried at equivalent distances.

c) 15 μg anti-VS antibody are placed in the central well and 7 to 22 μg of the $(VS)_{15}$ BSA complex and/or of the $(VS)_8$ PA complex are placed in the peripheral wells.

d) after diffusion for 12 h at room temperature, the plate is washed with a NaCl solution at 0.9%, dried and stained with Coomassie blue (0.5% solution in MeOH:-$H_2O$:HAC:$CHCl_3$=42.5:45:10:2.5).

2) ELISA a) a 96-wells microtitration plate (Flow Laboratories) is coated with 0.5 mg of either $(VS)_{15}$ BSA (FIG. 5) or $(VS)_8$ PA (FIG. 6) or BSA alone. This step is carried out at 4° C. for 12 h, in the presence of 1% glutaraldehyde in 0.15M NaCl.

b) excess complex is discarded.

c) the plate is saturated (1 h, at room temperature) with 1 mg/ml lactalbumin solution in buffer B (0.15M NaCl, 0.05% (v/v) Tween 80, 0.15M phosphate buffer pH 7.2).

d) the plate is washed fivefold with bufferB.

e) 50 ul of serial dilutions of either total or purified anti-VS antibodies (in NaCl at 0.9%) are added to each well. The plate is incubated for 1 h at room temperature.

f) the plate is fivefold washed with buffer B.

g) 50 μl of a 1/800 dilution of peroxidase-labeled anti-rabbit IgG are added in each well. The plate is incubated for 1 hour at room temperature.

h) the plate is once more washed with buffer B.

i) 50 μl of a 0.2% solution of orthophenylene-diamine in 0.015% $H_2O$; 15 mM citric acid, 60 mM phosphate buffer pH 6.3 are finally added, in each well and the plate is incubated 30 min at 37° C. in dark.

l) the reaction is stopped with 50 μl 4.5M $H_2SO_4$ in each well.

m) the optical density of each well is measured at 492 nm with a spectrophotometric reader for Elisa plates (Kontron Analytical SLT 210).

EXAMPLE 4

Affinity labelling of 70S ribosomes by the activated ester of virginiamycin S

A. Specific binding of virginiamycin S activated ester to 70S ribosome

Virginiamycin S is fluorescent in aqueous solutions containing bivalent ions such as $Mg^{++}$ or $Ca^{++}$. The increase of fluorescence intensity of virginiamycin S, accompanying its binding to the ribosome, is exploited to measure the association constant of the formed complex, the stoichiometry of the reaction, and the synergistic effect of virginiamycin M which causes a sixfold increase of the association constant of VS.

Moreover, when the VS.ribosome complex is incubated with erythromycin or other macrolide, the kinetics of the virginiamycin S displacement from the complex can be monitored (decrease of fluorescence).

These two approaches performed with the activated ester of virginiamycin S indicate an association constant very close to that of virginiamycin S ($1.5\times10^6 M^{-1}$ and $2.5\times10^6 M^{-1}$, respectively), that its stoichiometry was always 1:1, and that erythromycin also displaces the activated ester of virginiamycin S. These reaction takes place in a minute time, whereas the covalent binding requires a lapse of time tenfold to twentyfold longer.

These results indicate that virginiamycin S and the derivative "activated ester" share the same binding site on ribosomes.

B. Specific coupling of virginiamycin S to 70S ribosomes

This coupling reaction is made by use of the activated ester of virginiamycin S. In fact, a large number of ribosomal $NH_2$-lys and NH-his groups are liable to react with that derivative.

Moreover, the probability of occurrence of lysine or histidine residues in the neighbourhood of the VS binding site is high, because these residues represent 10 to 20% of total ribosomal protein residues.

1) Material 70S ribosomes from E. coli are obtained by Tissiéres' procedure: 1 optical density (O.D.) of ribosomes 70S at 260 nm corresponds to 24 pmoles.

The used erythromycin is a Boehringer product.

2) Method 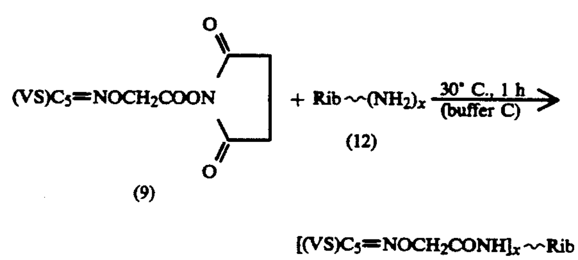 (9) (12) (13)

a) 5 nmoles 70S ribosomes are reactivated 5 min at 40° C. in 1 ml buffer C (10 mM $MgCl_2$, 50 mM TEA pH 7.8, 100 mM KCl, 4% EtOH).

b) Reaction 1

5 nmoles reactivated 70S are treated with 50 nmoles VS ester. The formation of the complex is carried out for 5 min at 4° C. The reaction is incubated for 1 h at 30°

C. in dark, then halted with 500 nmoles ethanolamine and incubated 15 min at room temperature.

Reaction 2

5 nmoles reactivated 70S are treated with 50 nmoles of Ery (saturation of the VS binding site) for 5 min at 4° C. 50 nmoles VSE are then added, and the mixture is incubated in dark: at 4° C. for 5 min and at 30° C. for 1 h. Reaction is halted as in 1.

Reaction 3

5 nmoles reactivated 70S are treated 5 min at 4° C. with 50 nmoles VS ester (previously hydrolyzed 1 h at 30° C. with 2500 nmoles ethanolamine). The mixture is then incubated at 30° C. for 1 h in dark. The reaction is stopped as in 1.

3) Purification of Rib VS

After completion of each reaction, 5 nmoles Ery are added (10 min, 30° C.) in order to displace the VS excess not covalently linked to the ribosome.

Each of the 3 samples is loaded (1, 2, 3) on a Sepharose 4B column (25 ml) and eluted with buffer C.

The fractions of 1 ml are collected for measurement at 260 nm. Fluorescence (as in II, C, 2) is also measured. The fractions containing the ribosomes (DO>0, F>0) are pooled and precipitated by addition of 0.7 volume EtOH, centrifugated at 5000 rpm for 10 minutes. The supernatant is discarded and the residue is resuspended in 1 ml buffer C (steps repeated twice: precipitation, centrifugation).

The affinity labeling of ribosomes by the activated ester of virginiamycin S is performed as such (panel A) or after saturation of the binding site by erythromycin (panel B). The first one refers to a total labeling (a nonspecific part+a specific part), the second one corresponds only to a non-specific labeling.

Panel C represents a control sample wherein the activated ester of virginiamycin S has previously been hydrolysed by ethanolamine.

The reaction mixtures are then fractionated by chromatography on a Sepharose 4B column.

The absorbance (A260 nm, —O—) and fluorescence (— —) of each fraction are measured as in IV, B, 3.

Figure 8:
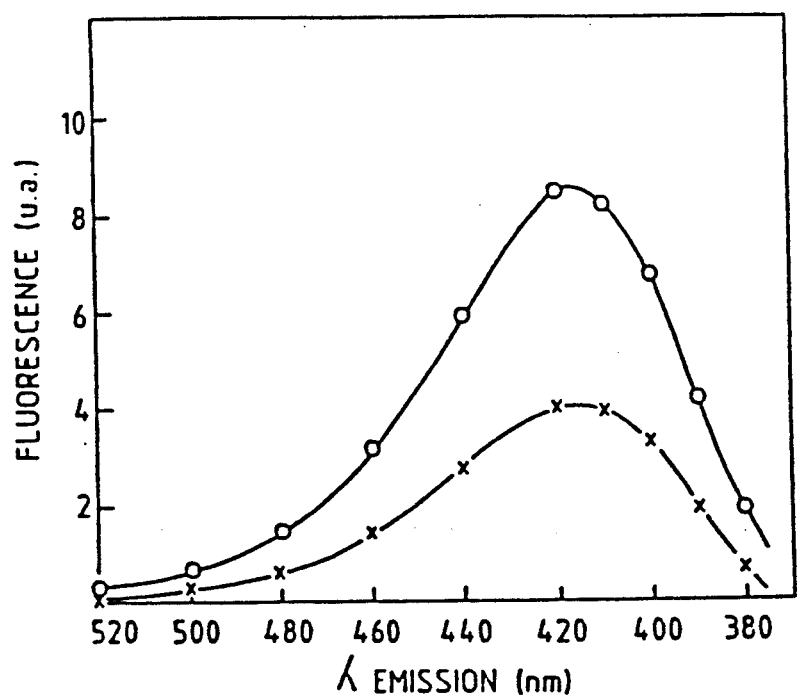

4) Evaluation of the coupling yield (FIG. 8).

10 O.D. units of purified ribosomes (correspond to 240 pmoles) from reaction 1 and 2 were diluted to 1 ml with buffer C. The fluorescence emission spectrum of both samples is then measured between 370 and 520 nm with λ excitation at 330 nm. The fluorescence shown the presence of VS in the sample. The obtained coupling yields are 1.5 moles VS/1 mole ribosome for reaction 1 (specific+non-specific) and 0.6 moles VS/1 mole ribosome for reaction 2 (non-specific).

Figure 7C:
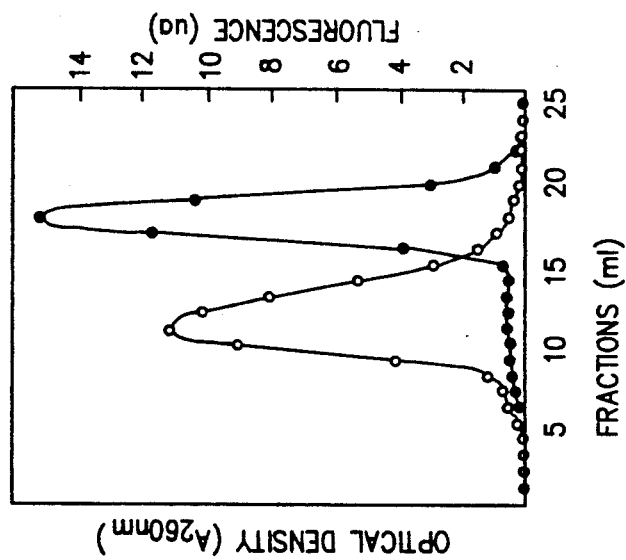
Figure 7B:
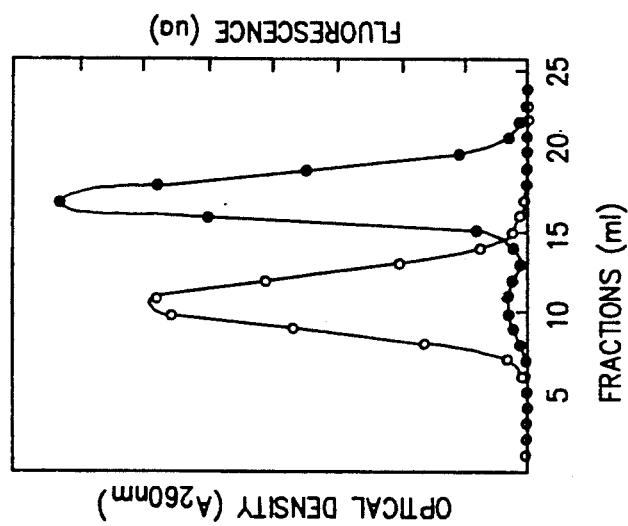
Figure 7A:
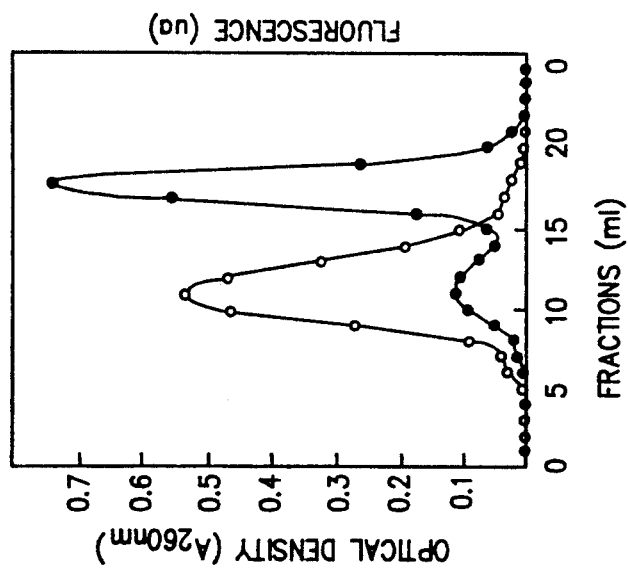

After purification of samples from both labelings (non-specific+specific) and (non-specific alone), as described with reference to FIG. 7, the fractions containing the ribosomes are pooled.

The amount of VS present at a known ribosome concentration is measured spectrofluorimetrically (λexc=330).

Curve (—O—) corresponds to the first type of labeling (non-specific+specific), the curve (— —) corresponds to the second type of labeling (non-specific only).

Compared to a blanc of VS, the coupling yields are evaluated to 1.5 and 0.6 moles VS/1 mole ribosome, respectively.

5) Extraction of ribosomal proteins

Ribosomal proteins are obtained by acetic acid extraction according to Hardy et al.

Figure 9:
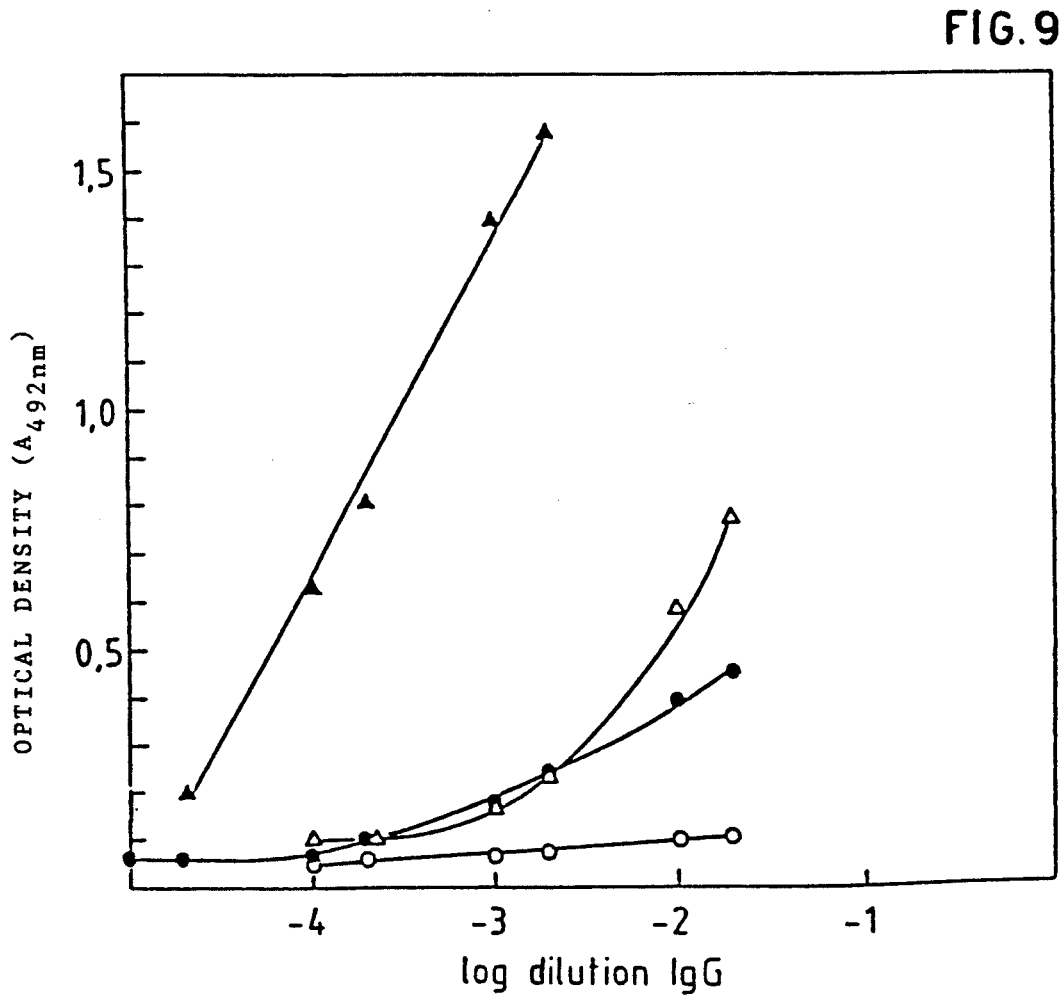

6) Elisa. (FIG. 9)

Elisa is carried out by the method already described here above on controle ribosomes 70S and on ribosomal proteins extracted therefrom. It is also carried out on ribosomes 70S-VS obtained after purification of reaction 1 and on ribosomal proteins extracted therefrom.

Figure 5:
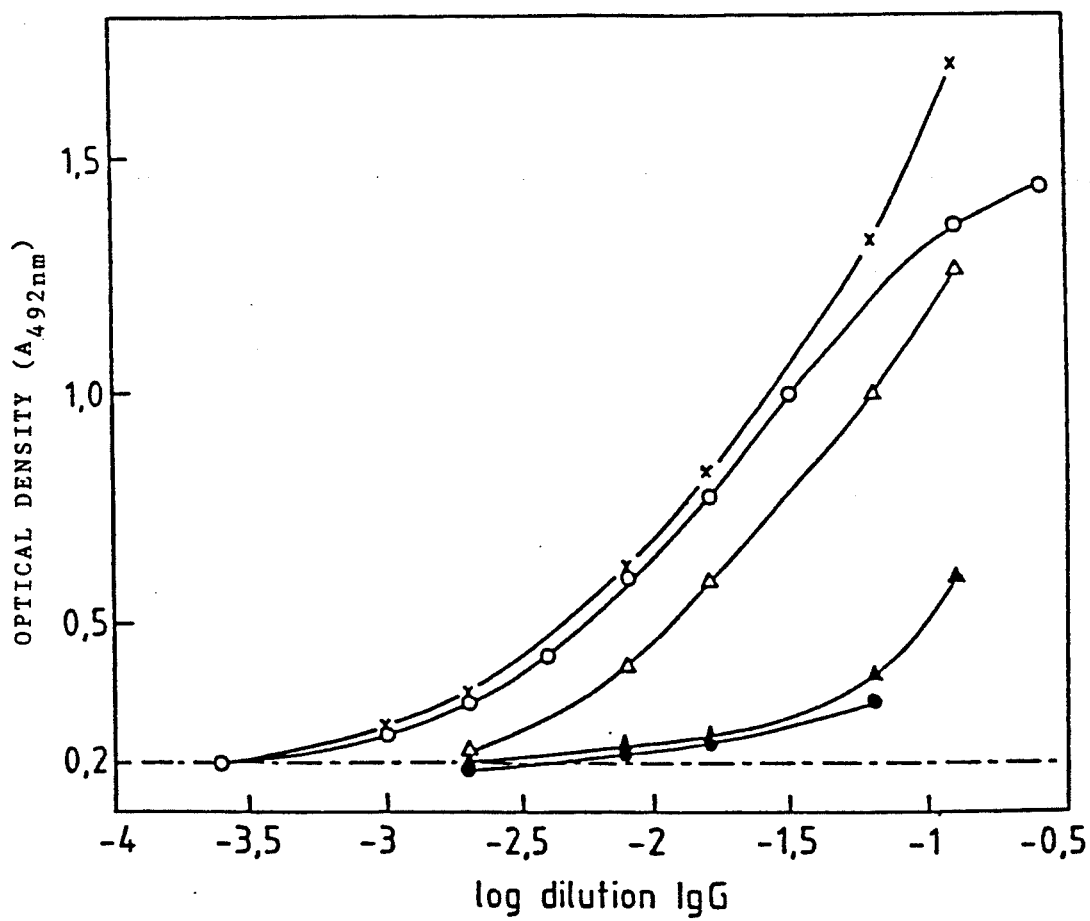
Figure 6:
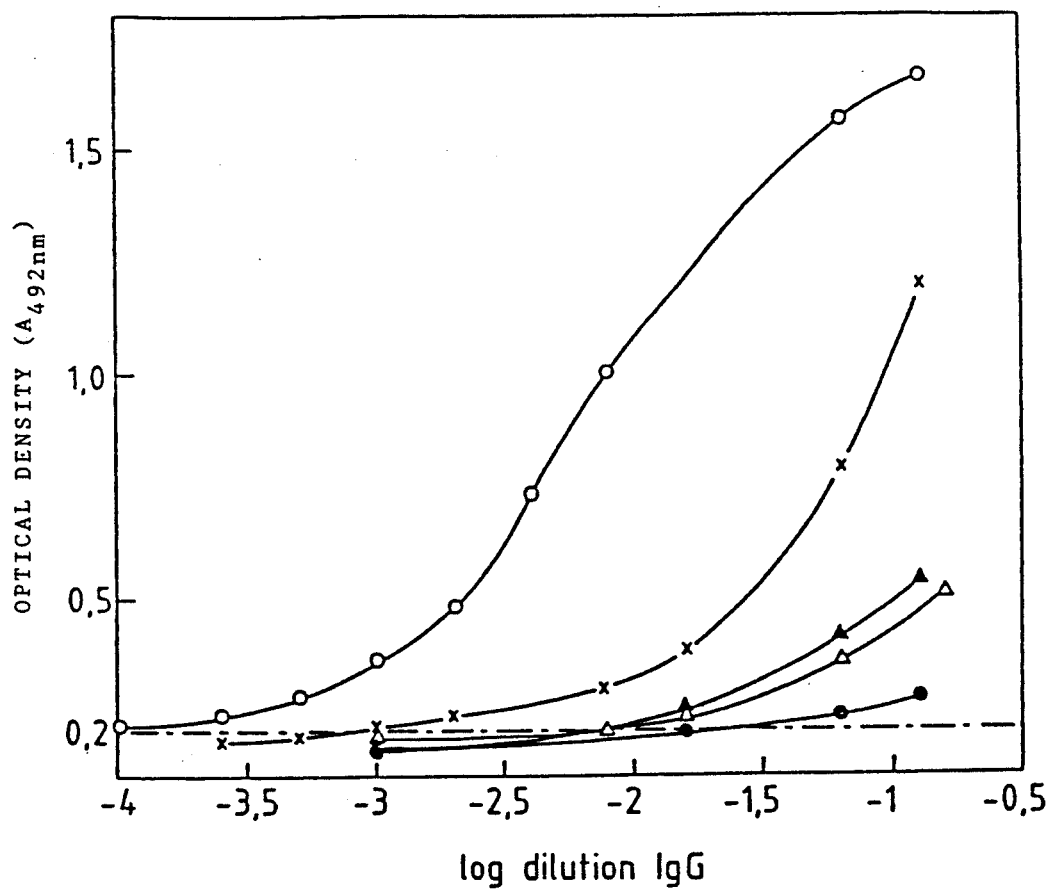

The enzymatic determination (Elisa) is performed as described in FIG. 5.

The purified ribosomal proteins from 10 pmoles ribosomes labeled by the activated ester of virginiamycin (— —) and non-labeled controls (—Δ—) are used as antigens.

The graph shows also the possible reaction of labeled ribosomal particles (— —) and ribosomal control particles.

EXAMPLE 5

The same reaction scheme as that of example 1 has been applied to the synthesis of a VS derivative carrying a (α-NH$_2$).COOH function. The reagent used for this reaction, canaline, has the structure:

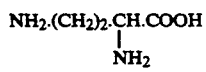

The product obtained

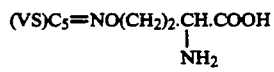

carries an alkaline and an acid group and can thus be linked to a series of —NH$_2$ and —COOH reagents. Let us cite, for instance, the reaction of lactobionic acid with the —NH$_2$ group of the above VS derivative. Other example is that of the coupling of D-glutamin with the —COOH of the activated VS ester. Both types of derivatives are endowed with solubilities in aqueous media and partition coefficients different from those of VS.

Consequently, according to the present application, the inventors have succeeded in grafting in one single step (antibiotic+reagent) to a portion of the specific antibiotic an arm carrying a terminal functional group, which is susceptible to undergo in a second step a reaction with different natural or synthetic compounds (aminoacids, sugars, proteins...). A series of derivative of this antibiotic can thus be obtained.

Therefrom result the following advantages:

The products obtained in the first reactional step (oximation of the ketonic function) are stable in aqueous media, contrarily to the products synthesized by means of the reagents of the type NH$_2$—(CH$_2$)$_n$—X (amines).

It is further possible to easily modulate the terminal function by means of different oxoaminated derivatives (NH$_2$O—(CH$_2$)$_n$—NH$_2$, NH$_2$O—(CH$_2$)$_n$—COOH ...).

Reaction yields are close to 100% and parasite side reactions are negligible (<5%).

Chemical group at the chain end can also be modified easily.

In their application, applicants have described the synthesis of the activated ester of virginiamycin S as well as the reaction of the latter with a macromolecule (BSA) in order to show the easiness of the technic.

The reaction with BSA has been presented as an example and not as a specific aim of this invention. Further, the possibility to prepare specific antibodies clearly shows the stability of the linkage between the antibiotic and the vector protein.

As comparison, the use of derivatives of types

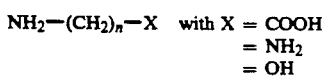

with X = COOH
= NH$_2$
= OH or NH$_4$Ac, NH$_2$—NH$_2$ ... always leads to mixtures of several products with yields lower than 60%.

The products thus obtained are generally unstable in aqueous media and regenerate the starting reagents (hydrolysis-equilibrated reaction).

We claim:

1. Derivatives of synergimycin according to the formula

where Z is a synergimycin radical of type A or B which is linked through its reactive carbonyl, by means of an arm X of the type =N— or =N—O—, to a substituent R representing a hydrogene atom, an alkyl group, an alkyl-COOH group, a group -alkyl-(α-NH$_2$)COOH, a group

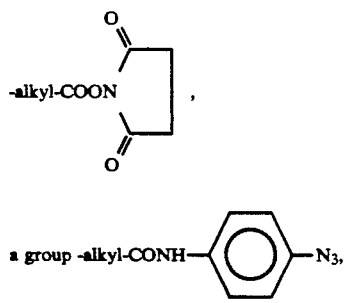

a group -(Alk-CONH)$_n$ Prot, or a group -(Alk-CONH)$_n$ Rib, where n is a function of the —NH$_2$ content of the coupling protein as well as pharmaceutically acceptable salts, esters and optionally, acid addition compounds with pharmaceutically acceptable acids.

2. Derivatives of synergimycin according to claim 1 wherein Z is the virginiamycin M radical according to the formula

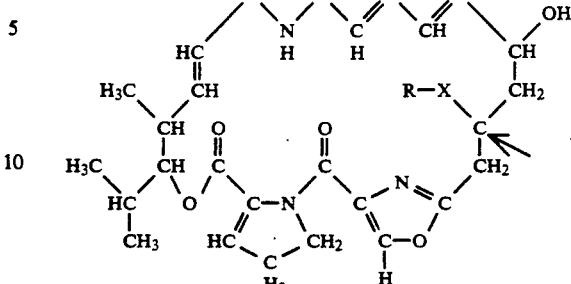

and the virginiamycin S radical, corresponding to the formula

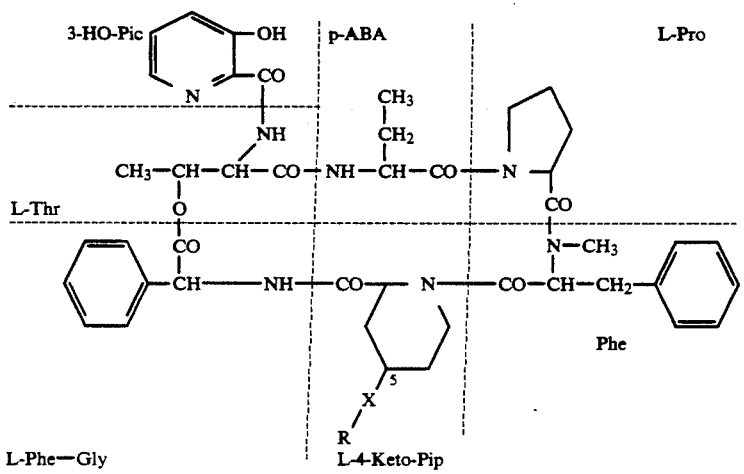

X and R being defined as here above.

3. Process for the preparation of the derivatives of synergimycin according to claim 1, characterized in that a compound of the type NH$_2$—R or NH$_2$—O—R wherein R represents a hydrogen atom, a linear or branched alkyl group, an alkyl-COOH group is reacted with the starting product(s) obtained by streptomycetes at a temperature of 20°–30° C., preferably of about 20° C., for 1 to 2 hours, preferably 4 hours, in pyridine medium.

4. A derivative according to claim 2 characterized in that the derivative is reacted with a compound of the type:

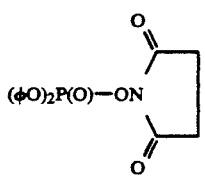

at a temperature of between 10° and 30° C., preferably about 20° C., for about 12 to 48 hours, preferably for 24 hours, in the presence of triethylamine.

5. A derivative according to claim 4 wherein the obtained product is reacted with any compound carrying a —NH$_2$ functionality.

6. Pharmaceutical preparation containing the derivatives according to claim 1, either individually or in combination with one another, optionally in combination with other compatible pharmaceutically acceptable active principles, vehicles, excipients and/or solvents.

7. Process for the preparation of the derivatives of synergimycin according to claim 2, characterized in that a compound of the type $NH_2$—R or $NH_2$—O—R wherein R represents a hydrogen atom, a linear or branched alkyl group, an alkyl-COOH group is reacted with the starting product(s) obtained by streptomycetes at a temperature of 20°–30° C., preferably of about 20° C., for 1 to 2 hours, preferably 4 hours, in pyridine medium.

8. Pharmaceutical preparation containing the derivatives according to claim 2, either individually or in combination with one another, optionally in combination with other compatible pharmaceutically acceptable active principles, vehicles, excipients and/or solvents.

9. Pharmaceutical preparation containing the derivatives produced by the process of claim 3, either individually or in combination with one another, optionally in combination with other compatible pharmaceutically acceptable active principles, vehicles, excipients and/or solvents.

10. Pharmaceutical preparation containing the derivatives of claim 4, either individually or in combination with one another, optionally in combination with other compatible pharmaceutically acceptable active principles, vehicles, excipients and/or solvents.

11. Pharmaceutical preparation containing the derivatives of claim 5, either individually or in combination with one another, optionally in combination with other compatible pharmaceutically acceptable active principles, vehicles, excipients and/or solvents.

12. A method of treatment of microbic disease in an animal, comprising administering to said animal, a pharmaceutical preparation in accordance with claim 6.

13. A method of treatment of microbic disease in an animal comprising administering to said animal, a pharmaceutical preparation in accordance with claim 9.

14. A method of treatment of microbic disease in an animal, comprising administering to said animal, a pharmaceutical preparation in accordance with claim 9.

15. A method of treatment of microbic disease in an animal, comprising administering to said animal, a pharmaceutical preparation in accordance with claim 10.

16. A method of treatment of microbic disease in an animal, comprising administering to said animal, a pharmaceutical preparation in accordance with claim 11.

17. A method according to claim 12 wherein said animal is a human animal.

18. A method according to claim 13 wherein said animal is a human animal.

19. A method according to claim 14 wherein said animal is a human animal.

20. A method according to claim 15 wherein said animal is a human animal.

21. A method according to claim 16 wherein said animal is a human animal.

* * * * *